United States Patent
Duarte (10) Patent No.: US 12,136,074 B2
(45) Date of Patent: Nov. 5, 2024

(54) DIGITAL NETWORK MARKETPLACE

(71) Applicant: Centro de Pesquisas Avançadas Wernher von Braun, Campinas-SP (BR)

(72) Inventor: Diego Daniel Duarte, São Carlos (BR)

(73) Assignee: CENTRO DE PESQUISAS AVANCADAS WERNHER VON BRAUN (BR)

( * ) Notice: Subject to any disclaimer, the term of this patent is extended or adjusted under 35 U.S.C. 154(b) by 110 days.

(21) Appl. No.: 17/412,535

(22) Filed: Aug. 26, 2021

(65) Prior Publication Data
US 2023/0069258 A1    Mar. 2, 2023

(51) Int. Cl.
*G06Q 20/12*      (2012.01)
*G06F 16/27*      (2019.01)
(Continued)

(52) U.S. Cl.
CPC ......... *G06Q 20/1235* (2013.01); *G06F 16/27* (2019.01); *G06F 16/9535* (2019.01);
(Continued)

(58) Field of Classification Search
CPC .............. G06Q 20/1235; G06Q 20/02; G06Q 20/3829; G06Q 20/389; G06Q 30/0631;
(Continued)

(56) References Cited

U.S. PATENT DOCUMENTS

| 11,017,329 B2 | 5/2021 | Augustine et al. |
| 11,018,851 B2 | 5/2021 | Sarin |

(Continued)

FOREIGN PATENT DOCUMENTS

| WO | WO-2018100371 A1 * | 6/2018 | ............ G06Q 20/02 |
| WO | 2020060868 A1 | 3/2020 | |

OTHER PUBLICATIONS

Dutta et al., A distributed ledger management mechanism for storing and selling private data, Feb. 10, 2021, IEEE, DOI: 10.1109/DSC49826.2021.9346258 (Year: 2021).*

*Primary Examiner* — Courtney P Jones
*Assistant Examiner* — Christine Dang
(74) *Attorney, Agent, or Firm* — Jon Gibbons; Fleit Intellectual Property Law (57) ABSTRACT

A computing device and computer-implemented method to provide access to a private data object is described. The system uses Non-Fungible Tokens (NFT) and smart contracts as a mechanism to provide access to data. The information to which the token refers, e.g., the artwork, is viewable by everyone as part of a digital ledger network. The token is used only to determine who owns that item. The present approach offers an alternative for using NFT, so that access to the information itself to which the token is linked is controlled and negotiated by the token owner. The present invention can be applied to any IoT network that performs data collection that is of interest to companies or organizations outside the network in which the collection was performed, allowing to identify the ownership of IoT devices. Thus, enabling access control to the device's data, by their owners, directly through the blockchain.

20 Claims, 8 Drawing Sheets

(51) Int. Cl.
  *G06F 16/9535* (2019.01)
  *G06F 21/60* (2013.01)
  *G06Q 20/02* (2012.01)
  *G06Q 20/38* (2012.01)
  *G06Q 30/0601* (2023.01)
  *G06Q 40/02* (2023.01)
  *G16H 10/60* (2018.01)

(52) U.S. Cl.
  CPC .......... *G06F 21/602* (2013.01); *G06Q 20/02* (2013.01); *G06Q 20/3829* (2013.01); *G06Q 20/389* (2013.01); *G06Q 30/0631* (2013.01); *G06Q 40/02* (2013.01); *G16H 10/60* (2018.01)

(58) Field of Classification Search
  CPC ..... G06Q 40/02; G06F 16/27; G06F 16/9535; G06F 21/602; G16H 10/60
  See application file for complete search history.

(56) References Cited

U.S. PATENT DOCUMENTS

| | | | |
|---|---|---|---|
| 11,501,370 B1* | 11/2022 | Paya | G06Q 20/3676 |
| 2001/0047282 A1* | 11/2001 | Raveis, Jr. | G06Q 30/0245 |
| | | | 707/999.009 |
| 2007/0244809 A1* | 10/2007 | Meeks | G06Q 20/26 |
| | | | 705/39 |
| 2009/0240627 A1* | 9/2009 | Rodriguez | H04L 9/321 |
| | | | 705/76 |
| 2015/0058150 A1* | 2/2015 | Gura | G06Q 30/0601 |
| | | | 705/26.3 |
| 2016/0026983 A1* | 1/2016 | Lindsley | G06Q 30/0635 |
| | | | 705/26.81 |
| 2016/0260171 A1* | 9/2016 | Ford | G06Q 20/389 |
| 2018/0040040 A1 | 2/2018 | Barski et al. | |
| 2018/0218455 A1 | 8/2018 | Kolb et al. | |
| 2019/0205563 A1 | 7/2019 | Gonzales, Jr. | |
| 2020/0058023 A1 | 2/2020 | Travizano et al. | |
| 2020/0090188 A1 | 3/2020 | Wince et al. | |
| 2021/0279305 A1* | 9/2021 | Goldston | H04L 9/50 |
| 2022/0013226 A1* | 1/2022 | Nag | G16H 40/67 |
| 2022/0414809 A1* | 12/2022 | Geng | H04L 9/50 |

* cited by examiner

DIGITAL NETWORK MARKETPLACE

BACKGROUND

The present invention generally relates to the facilitation of data exchange through a digital network marketplace.

There is an ever-increasing amount of data gathered across a large number of sources and contexts. This increase is due to advancements in communications technologies, such as the Internet, wireless technologies, Wi-Fi, near-field communications, and 5G cellular combined with larger storage capacities at a lower cost and combined with a proliferation of data-gathering technologies. Data gathering technologies include sensors, implementations of the Internet of Things (IOT), and smartphones. For example, several sectors of the economy, including healthcare, logistics, transportation, fitness, smart buildings, automotive, use sensors to gather data. Personal devices that provide data include fitness trackers, smartwatches, and other mobile devices with built-in sensors to measure location, record pictures, record sound, measure temperature.

Large quantities of data are commonly generated by individuals, corporations, collective organizations, universities, schools, and other entities. Data scientists often want access to these data to allow analysis. This data is applied to artificial intelligence, machine learning, and data mining to uncover correlations that may otherwise remain hidden.

Individuals are concerned about data privacy. The needs of researchers and others interested in processing, analyzing, and otherwise utilizing large stores of data are often at odds with popular desire and/or regulatory mandate for privacy. Additionally, the interactions between these different parties (entities who generate and/or store data, entities who recommend known data sets, and entities who desire access to the data) are regularly complicated by divergent business interests and/or a lack of trust. Moreover, decisions about the data that may need to be made by one party often require information held by another party, and the common channels for requesting and providing such information can be frustratingly slow and unreliable. In addition, the process of determining what information about the data may be needed, requesting that information from another party, waiting for the information, receiving and evaluating it to finally render a decision often makes standard data exchange processes slow to a crawl and provides many opportunities for problems and disagreements to arise.

Currently, several sectors of the economy, such as automotive, logistics and industry, use sensors to collect IoT information, information that is used to configure, optimize and make decisions about the operation performed by these companies. Much of this information, however, may be of interest not only to the company that owns the sensors but also to its customers, insurers, professional bodies, among other examples.

SUMMARY

The present invention overcomes limitations with prior art systems by providing a system that used uses Non-Fungible Tokens (NFT) and smart contracts as a mechanism to provide access to data. The information to which the token refers, e.g., the information regarding the artwork is viewable by everyone as part of a digital ledger network. The artwork itself is not viewable by others. The token is used to determine who owns that item. The present approach offers an alternative for using NFT, so that access to the information itself to which the token is linked is controlled and negotiated by the token owner.

More specifically disclosed are a system and a computer-implemented method for providing access to a private data object. The method begins with receiving, from a seller, a data register request on a digital ledger network. The data register request is to sell access to the private data object stored in a seller's private digital collection. The private data object can be data from a sensor, a medical record, images, videos, or any other digital content and is referenced into the digital ledger network as a non-fungible token (NFT).

Next, in response to receiving the data register request, a public data object is created on a digital ledger network. The public data object provides details, including metadata about the private data object. The process continues to receiving a public selling order on the digital ledger network to sell access to the private data object. Next, in response to receiving the public selling order, a public selling object is created on the digital ledger network. The public selling object may include a purchase price to access the private data object. In addition to creating the public selling object, a public buying order is received from a buyer on the digital ledger network. The public buying order is used to purchase access to the private data object. The public buying order references the public selling object.

Next, in response to creating the public buying order, a first authorization is received on the digital ledger network from the buyer to authorize the purchase price to be debited from a buyer's account. Typically, this authorization authorizes only the selected or elected trusted operator to execute this debit.

Next, in response to receiving the first authorization, updating the public selling object on the digital ledger network to include a public purchase object, wherein the public purchase object references the buyer. Again, this updating only authorizes the selected or elected trusted operator to update the public selling object.

Next, in response to updating the public selling object, a second authorization is received from the seller on the digital ledger network to provide access to the private data object. Again, this updating only authorizes the selected or elected trusted operator to provide access to the public selling object.

Optionally, the buyer may search over the digital ledger network, for public selling orders. Furthermore, the method may include a data purchase interest request on the digital ledger network. The data purchase interest request is from the buyer and may include conditions to purchase access to the private data object. Also, optionally, in response to receiving the data purchase interest request, receiving, from the third-party or a delegate of the buyer, a recommendation of selling orders that matches the conditions to purchase access to the private data object.

Next, in response to the second authorization, copying the private data object stored in the seller's private digital collection to a third-party, and storing the private data object on a buyer's private digital collection, wherein the seller's private digital collection and the buyer's private digital collection are different digital collections. In one example, the purchase price to be debited from the buyer's account is divided into two payment parts, a first payment part paid to the third-party and a second payment part paid to the seller.

In response to the second authorization, the method may include copying the private data object stored in the seller's private digital collection to a third-party. The private data object may be encrypted with a first encrypting key, and decrypting the private data object using a first decrypting key of the seller, and re-encrypting the private data object using a second decrypting key of the buyer and storing a re-private data object on a buyer's private digital collection.

The method may be performed by the same entity that manages the third-party. The third-party, in one example, is the buyer or the seller. Also, the seller's private digital collection, the buyer's private digital collection, and the third-party are different entities.

In another example, the third-party is one of a plurality of third-parties, and the third-party is selected by the seller, the buyer, or both. Stated differently, any member of the blockchain network may be a "trusted third-party." It does not need any unique role. If the buyer and seller agree on a trusted third-party, this is all that is required. This agreement or election can occur on the fly. The seller may suggest the trusted third-party in a smart contract through a sell order, and the buyer agrees to the purchase order using smart contracts.

BRIEF DESCRIPTION OF THE DRAWINGS

In the accompanying figures, like reference numerals refer to identical or functionally similar elements throughout the separate views. The accompanying figures, together with the detailed description below, are incorporated in and form part of the specification and serve to further illustrate various embodiments and to explain various principles and advantages, all in accordance with the present invention, in which.

DETAILED DESCRIPTION

Disclosed is a system that uses Non-Fungible Tokens (NFT) and smart contracts as a mechanism to provide access to data. The information to which the token refers, e.g., the artwork is viewable by everyone as part of a digital ledger network. The token is used only to determine who owns that item. The present approach offers an alternative for using NFT, so that access to the information itself to which the token is linked is controlled and negotiated by the token owner.

The present patent can be applied to any IoT network that performs data collection that is of interest to companies or organizations outside the network in which the collection was performed, allowing to identify the ownership of IoT devices. Thus, enabling access control to the device's data, by their owners, directly through the blockchain.

As a non-limiting example, let's say we have a blockchain with a seller named Diego and a purchaser named Jon as registered participants. In this example, Diego has a video to sell access to as a digital data object. Diego could advertise the availability of this video either on or off the blockchain. The advertisement may be "I want to sell access to this video for $20". So, Jon responds, "Ok. I want to buy it". However, there is a trust problem between Diego and Jon. Diego does not trust Jon will pay him after Diego grants Jon access to the video. Therefore, Diego will not grant Jon access before Diego receives payment from Jon. Conversely, Jon does not trust Diego will grant Jon access after Jon pays Diego. Jon will not pay Diego before Diego gives Jon access.

To solve this problem, one example of the present invention provides, when Jon replies "Ok. I want to buy it", Jon will also clarify with "Since we both don't trust each other, I propose trusted third-party, named Marcela, to handle the transaction." In the case in which Diego trusts Marcela will grant Jon access to the video, and, so, Jon is willing to pay Marcela before Jon receives access to the video. Jon will allow Marcela to debit $20 from Jon's account. Suppose that Diego also trusts Marcela will pay him after Diego grants Marcela access to the video. In that case, Diego will accept the proposal from Jon and grant access to the video to Marcela. Marcela now became the "trusted third-party" or, more specifically, the "elected third-party" or "elected operator" or "elected trust operator." She will copy the video to Jon and also pay Diego.

However, if Diego does not trust Marcela will pay him after he grant her access to the video, Diego would refuse Jon's proposal. In this case Jon may then, for instance, reply with "Ok, how about Michael?". The process continues until both Diego and Jon agreed with the proposed trusted third-party, or Diego and Jon discover they do not have any mutually trusted person to operate the transaction.

Non-Limiting Definitions

The terms "a", "an" and "the" are intended to include the plural forms as well, unless the context clearly indicates otherwise.

The phrases "at least one of <A>, <B>, . . . and <N>" or "at least one of <A>, <B>, . . . <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N, that is to say, any combination of one or more of the elements A, B, . . . or N including any one element alone or in combination with one or more of the other elements which may also include, in combination, additional elements not listed.

The terms "comprises" and/or "comprising", when used in this specification, specify the presence of stated features, steps, operations, elements, and/or components, but do not preclude the presence or addition of one or more other features, integers, steps, operations, elements, components, and/or groups thereof.

The term "computing node" is used to mean computational device, such as a federation of computers or servers, with an internal address that can host a copy of a blockchain and the associated transactions.

The term "configured to" describes the hardware, software, or a combination of hardware and software that is adapted to, set up, arranged, built, composed, constructed, designed or that has any combination of these characteristics to carry out a given function. The term "adapted to" describes the hardware, software, or a combination of hardware and software that is capable of, able to accommodate, to make, or that is suitable to carry out a given function.

The term "coupled," as used herein, is defined as "connected," although not necessarily directly and not necessarily mechanically.

The term "data object" is any data, typically in a digital format, including texts, multimedia, film, pictures, sound recordings, games, software, health data, and more.

The term "digital ledger" or "distributed ledger technology (DLT)," as used herein, is a digital system for recording the transaction of assets in which the transactions and their details are recorded in multiple places at the same time. Unlike traditional databases, distributed ledgers have no central data store or administration functionality. Blockchain is a type of DLT where transactions are recorded with an immutable cryptographic signature called a hash.

The term "gossip protocol" or "epidemic protocol" is a procedure or process of computer peer-to-peer communication that is based on the way epidemics spread. Some distributed systems use peer-to-peer gossip to ensure that data is disseminated to all members of a group. Some ad-hoc networks have no central registry, and the only way to spread common data is to rely on each member to pass it along to their neighbors.

The term "hash function" is a mathematical algorithm that turns an arbitrarily-large amount of data into a fixed-length size. The same hash will always result from the same data, but modifying the data by even one bit will completely change the hash. The values returned by the hash function are called a "hash".

The terms "including" and "having," as used herein, are defined as comprising (i.e., open language).

The term "non-fungible token (NFT)" or, more simply, a "token" is a unit of data stored on a digital ledger, such as a blockchain, that certifies a digital asset to be unique and therefore not interchangeable. NFTs can be used to represent items such as photos, videos, audio, and other types of digital files.

The term "public data object" is a description including metadata regarding a data object.

The phrase "smart contract" is a self-executing contract with terms of the contract between a buyer and a seller directly written in lines of computer code or in a transaction protocol. The smart contract is designed to automatically execute, control, or document legally relevant events and actions according to the terms of a contract.

The term "trusted third-party" is an entity or individual capable of operating on the blockchain to receive payment from a purchaser, send payment to the seller, and copy the data object between the parties. The trusted third-party is selected or elected by both the seller and purchaser.

Blockchain Network Using NFTs

Figure 1:
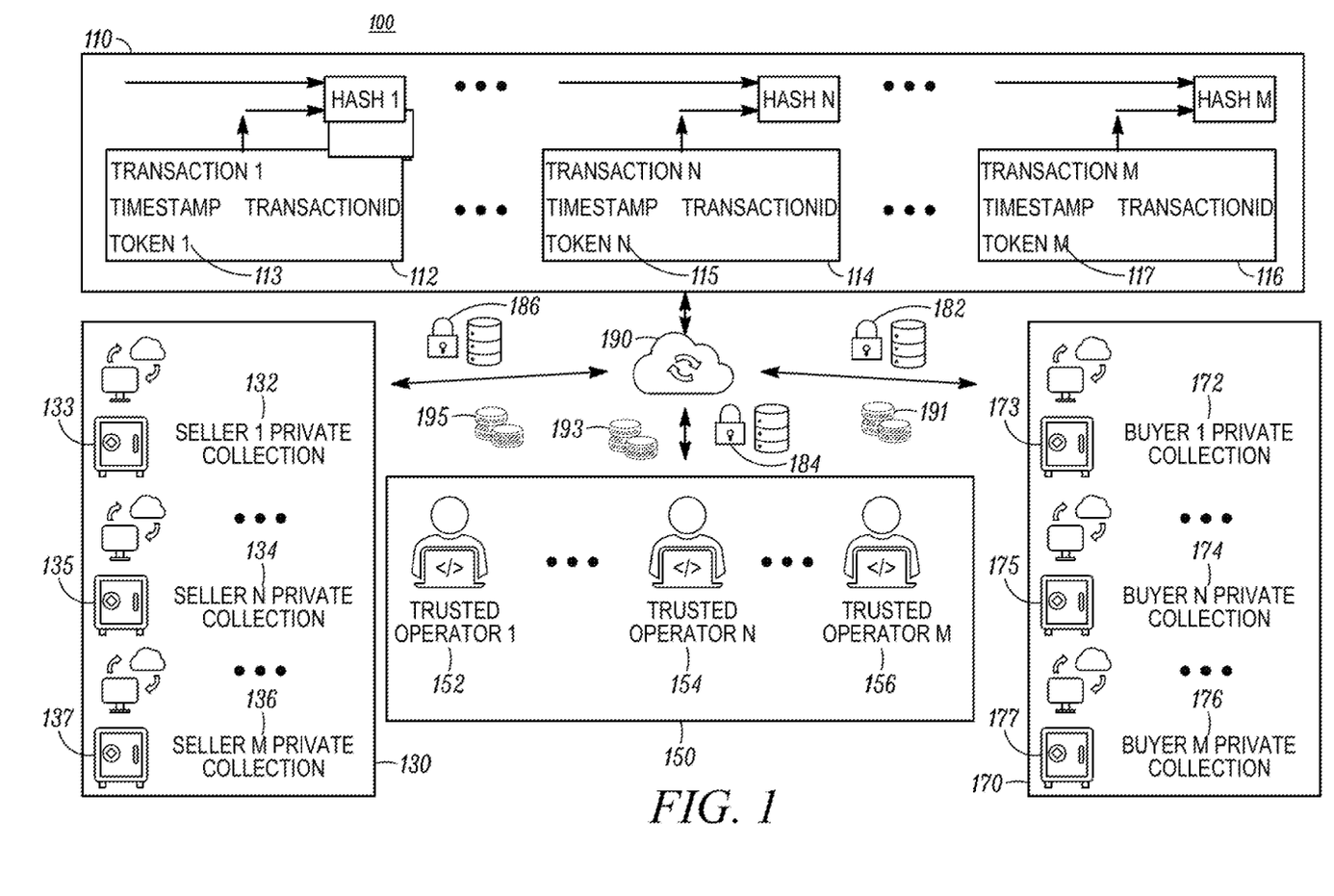
FIG. 1 is a high-level diagram for providing access to a private data object on a blockchain in accordance, in accordance with one aspect of the present invention.

FIG. 1 is a high-level diagram 100 for providing access to a private data object on a blockchain in accordance, in accordance with one aspect of the present invention. Shown are four major components 110, 130, 150, 170 all connected via a public network 190, such as the Internet. The first of the four major components is a blockchain 110 with a series of blocks 112, 114, 116. Each of the blocks 112, 114, 116 with tokens or NFTs 113, 115, 117 (Token 1, Token N, Token M) is shown. The second of the four major components are a group of sellers 130, with each of the sellers 132, 134, 136, in the group including a private collection 133, 135, 137 of data objects. The third of the four major components is a group of trusted operators 150. The trusted operators are entities 152, 154, 156, selected by the buyer and seller and typically independent of a buyer and a seller that carries out the transactions placed on the blockchain 110. The fourth of the four major components are a collection 173, 175, 177 of buyers 170, with each of the buyers 172, 174, 176, in the group including a private collection of data objects. All four of these four major components communicate over a network 190 using a combination of wired and wireless communications. In one example, only the trusted operators are able to write data in private collections 173, 175, 177 of the buyers 172, 174, 176 or the sellers 132, 134, 136. In another example, all parties are allowed to write data in all collections, but only the private collections owner is allowed to read those data. The tokens are used to reference data objects of the sellers 132, 134, 136 and the buyers 172, 174, 176, as will be further described below.

The process begins with one of the sellers 132, 134, 136 in the group of s sellers 130, offering access to one or more data objects in the seller's n Private Collection 113, 115, 117. The seller creates a 113 token 1 with a public data object that describes the Data Object to which access in the seller's n Private Collection is being offered. The access may be fee-based or no-fee, but the terms of the access are part of the token that is viewable by other participants on the blockchain 110. The terms of access may include one or more of exclusivity, a period of time granted for the access, restrictions on use, restrictions on re-distribution, restriction on performance or display in the case of copyrighted works, geographical limitations, privacy requirements, and more. The seller 132, 134, 136 creates an entry on the blockchain 110, referred to as a "Selling Order", that includes the 113 token 1 on the blockchain 110. The selling order also includes a timestamp, a transaction ID, and a hash of the previous block with the current block as shown. This ensures that there has been no tampering or alteration of the data in the record blockchain. Each block 112, 114, 116 on the blockchain 110, generally represented as part of a Merkle tree which is typical of blockchain protocols, such a Hyperledger, Quorum, Tezos, and others.

The transaction id can be searched for a specific item. The token includes the public data object describing the data object being offered for access. In one example, the token can also include an optional category. The optional category may be a photo, medical, financial, employment, etc., to associate with the access to the data object of the sellers to which access is being sold.

The tokens are used to reference a data object in a private collection 133, 135, 137 in one of the sellers 132, 134, 136 of the group of sellers 130. These private collections 133, 135, 137 are stored off the blockchain 110. In this example, blockchain 110 is used to record, document, and allow auditing of transactions related to access of data, but the data or data object itself is not stored on blockchain 110. The blocks 112, 114, 116 are recorded that confirm when and in what sequence certain transactions become journaled. As shown, the data in each of the seller's private collection in one of the sellers 132, 134, 136 of the group of sellers 130 is encrypted as shown graphically by the safe. In one example, each data object in each private collection is encrypted with its own unique key.

Next, one of the buyers 172, 174, 176 of the group of buyers 170, or a buyer's agent can peruse or look through the blockchain 110 for "Selling Order" from the group of sellers 130. In the event one of the buyers 172, 174, 176 of the group of buyers 170 is interested in a selling order, the buyer registers a "Purchase Order," which is associated with the selling order.

The buyer may also select a trusted operator 152, 154, 156 from the group of trusted operators 150. The trusted operator is typically an independent third party authorized to perform the transaction on the blockchain 110. In one example, the Selling Order itself may also include a list of trusted operators to carry out the operation. This may be accomplished using a smart contract. In another example, the buyer or the buyer's agent selects a trusted operator 152, 154, 156 from the list of trusted operators 150 authorized to perform the transaction, and the seller confirms. Once the trusted operator is confirmed, it will execute the buy-sell agreement between the seller and the buyer. If the smart contract or agreement requires payment from the buyer to access the data object located in the seller's private collection, the trusted third party will receive payment 191 from the buyer to hold in escrow. The escrow is a contractual arrangement in which a selected trusted third party receives and disburses money to seller 195 for the performing transaction. The disbursement depends on conditions agreed to by the transacting parties. The selected trust operator in one example as receives a portion 193 of the payment paid from the buyer to the seller.

Next, the selected trusted operator 152, 154, 156 reads the data object, which is the subject of the transaction from the seller's private collection 133, 135, 137. In one example, the data object is encrypted with a symmetrical key or public-private key pair 182. The selected trusted operator has access to the decrypting key 184. Operator decrypts and may re-encrypt the data object with a symmetrical key or public-private key pair 186 from the buyer before placing the data object in the buyer's Private Collection.

Storage Repository Details with Blockchain

Figure 2:
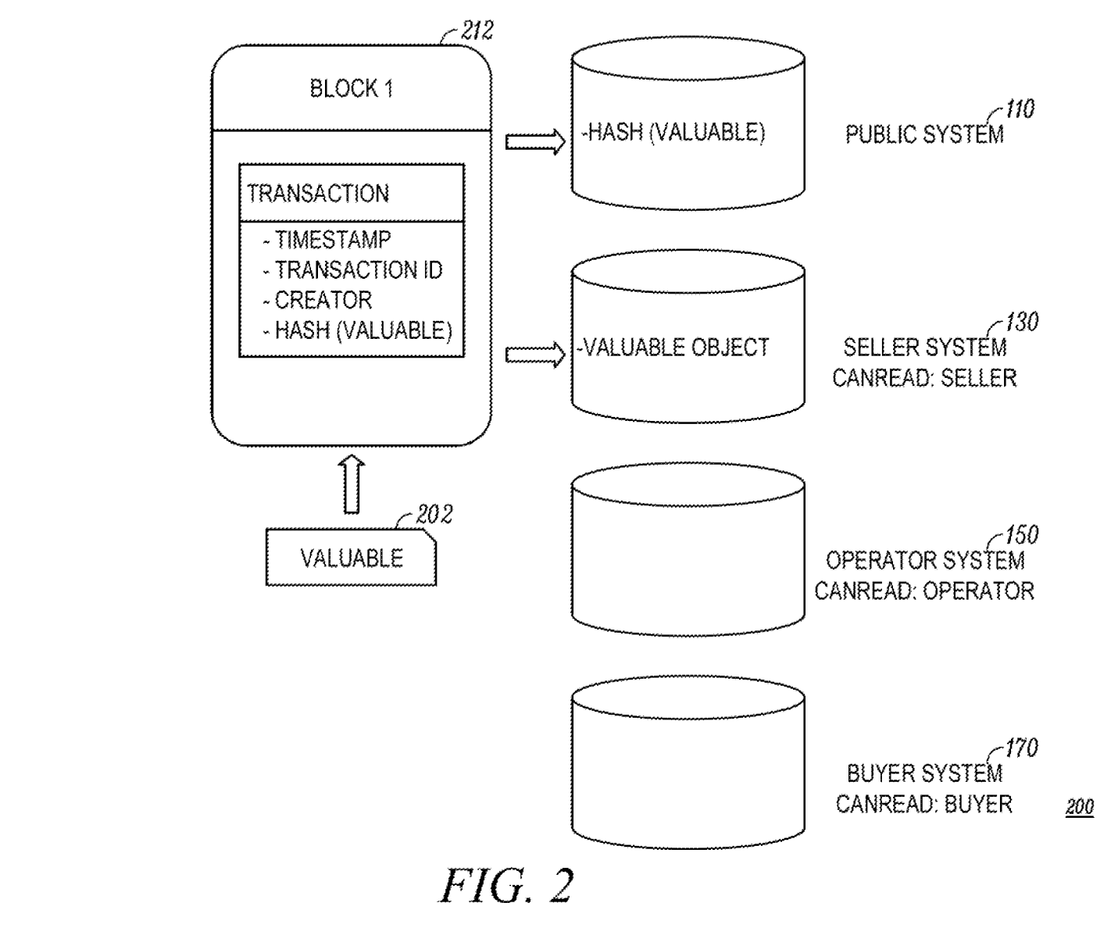
FIG. 2 through FIG. 6 are a series of diagrams illustrating the storage repository details with the blockchain in FIG. 1, in accordance with one aspect of the present invention.

FIG. 2 through FIG. 6 are a series of diagrams illustrating the storage repository details with the blockchain 110 in FIG. 1 in accordance with an example of the present invention. Although the block in these high-level diagrams 200, 300, 400, 500, 600 are shown as consecutive, in the implementation in which multiple parties are buying and selling, other intervening blocks not shown on the blockchain would be expected within the true scope of the present invention. Turning to FIG. 2, Block 1 212, shown is a seller placing public data object 202 onto a blockchain 110 for others authorized on the blockchain to see. The public data object 202 is not the data object itself, rather as described previously it contains metadata and conditions for gaining access, e.g., read access, to it. The process flows to Block 2 in FIG. 3.

Figure 3:
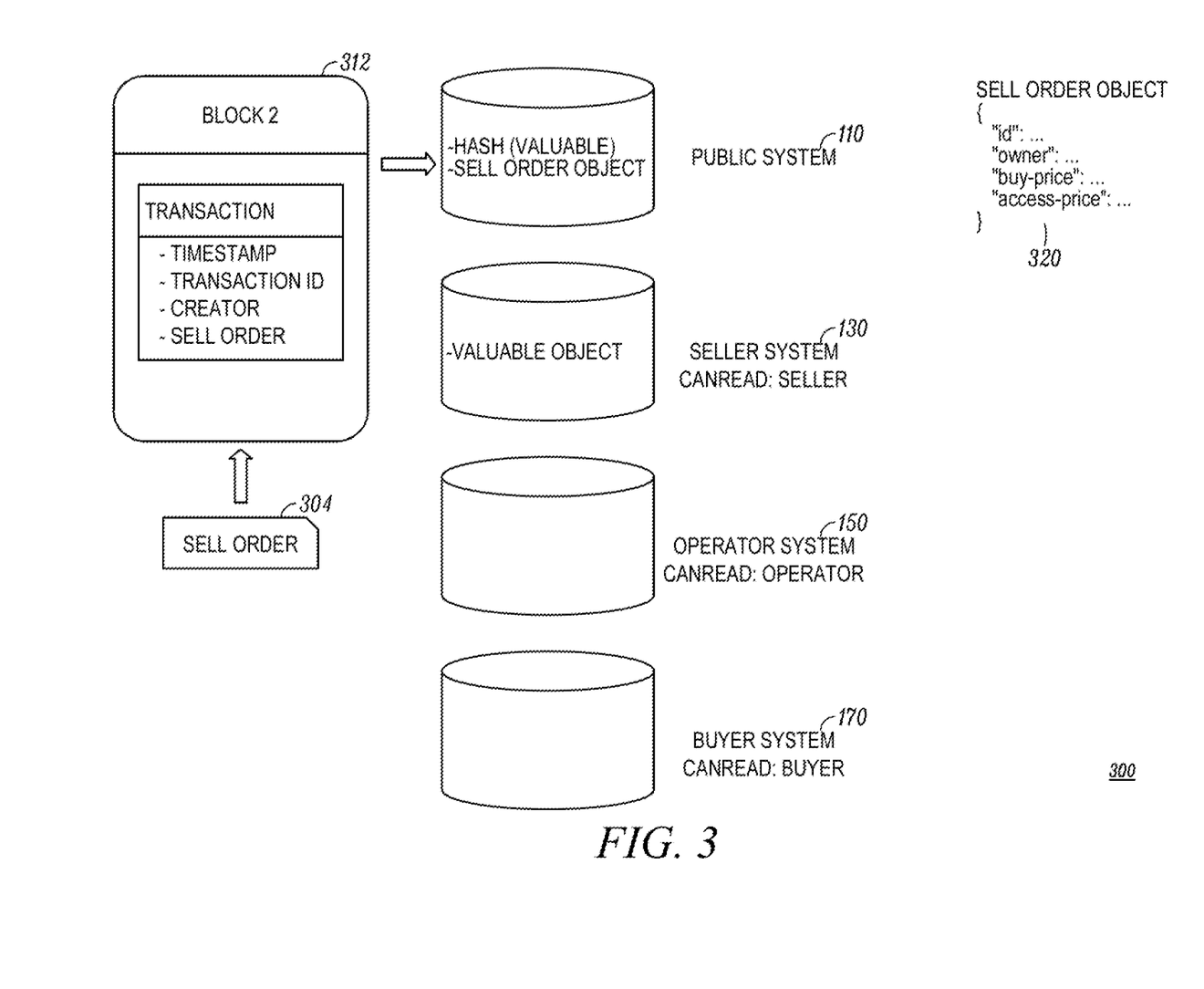

In FIG. 3, Block 2 312, using the public data object 202, a sell order 304 is created on the blockchain 110 from one of the sellers 132, 134, 136 from the group of sellers 130. The Sell Order 304 includes the information in public data object about a data object to which access is being offered and also includes terms and conditions about the offer may include a price. Other terms that may be embodied in a smart contract are exclusivity, a period of time granted for the access, restrictions on use, restrictions on re-distribution, restriction on performance or display in the case of copyrighted works, geographical limitations, privacy requirements, and more. One example of the sell order object is an instance of a particular class 320 or subclass with the class's own methods or procedures and data variables. The process continues to Block 3 in FIG. 4.

Figure 4:
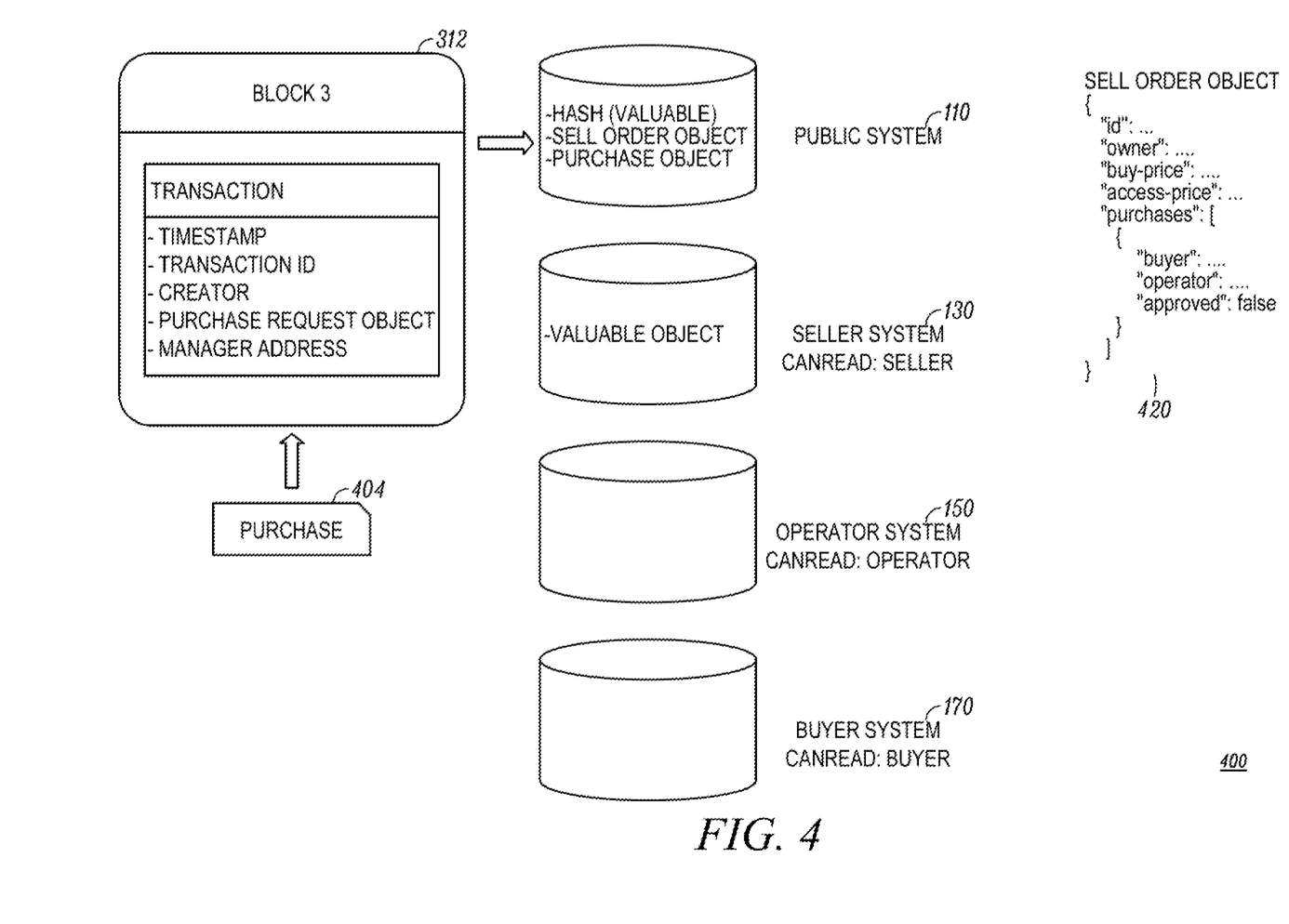

In FIG. 4, Block 3 412, a buyer 172, 174, 176 from the group of buyers 170, creates a purchase order object 206. The purchase order 404 may include an acceptance of a trusted operator 152, 154, 156 from the group of trusted operators 150 as specified in the sell order 304. Shown is the sell order object 320 of FIG. 3 is updated with the purchase order 404 as shown 420. The process continues to Block 4.

Figure 5:
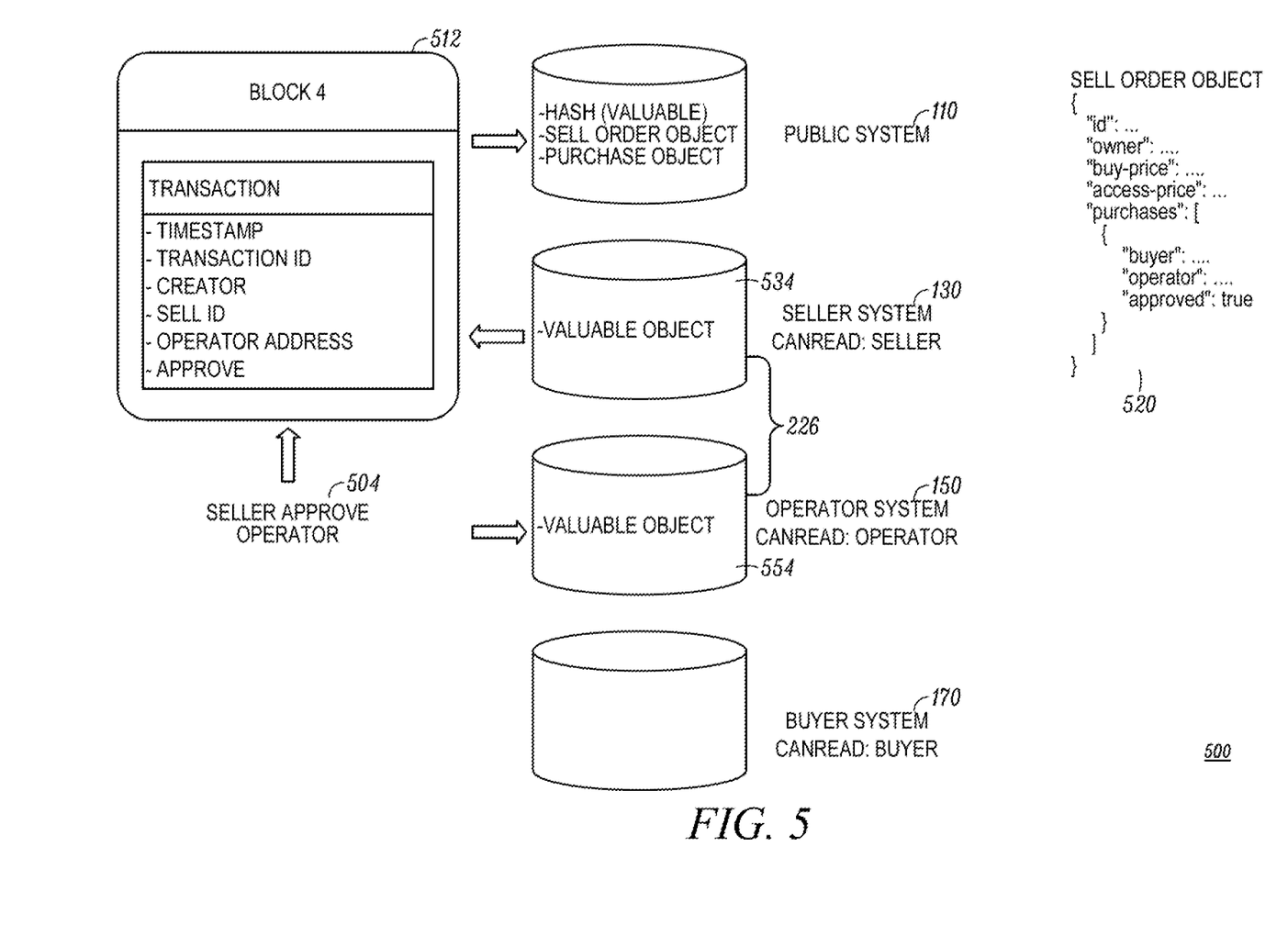

In FIG. 5, Block 4 512, the specific seller who placed the public data object 202, from the group of sellers 130, approves the proposed operator indicated by the buyer who created the purchase order object 206. In response to this approval, the data object, which is the subject of the transaction, is copied from one of the seller's private collection 133, 135, 137 to one of the Operator's Private Collection 173, 175, 177. The copying may include encrypting the data as described above. Shown is the sell order object 420 in FIG. 4 is updated with the approved field set to "true" as shown 520, and the data object 226 being copied from the seller's private collection 534 to the Operator's Private Collection 554. The process continues to Block 5.

Figure 6:
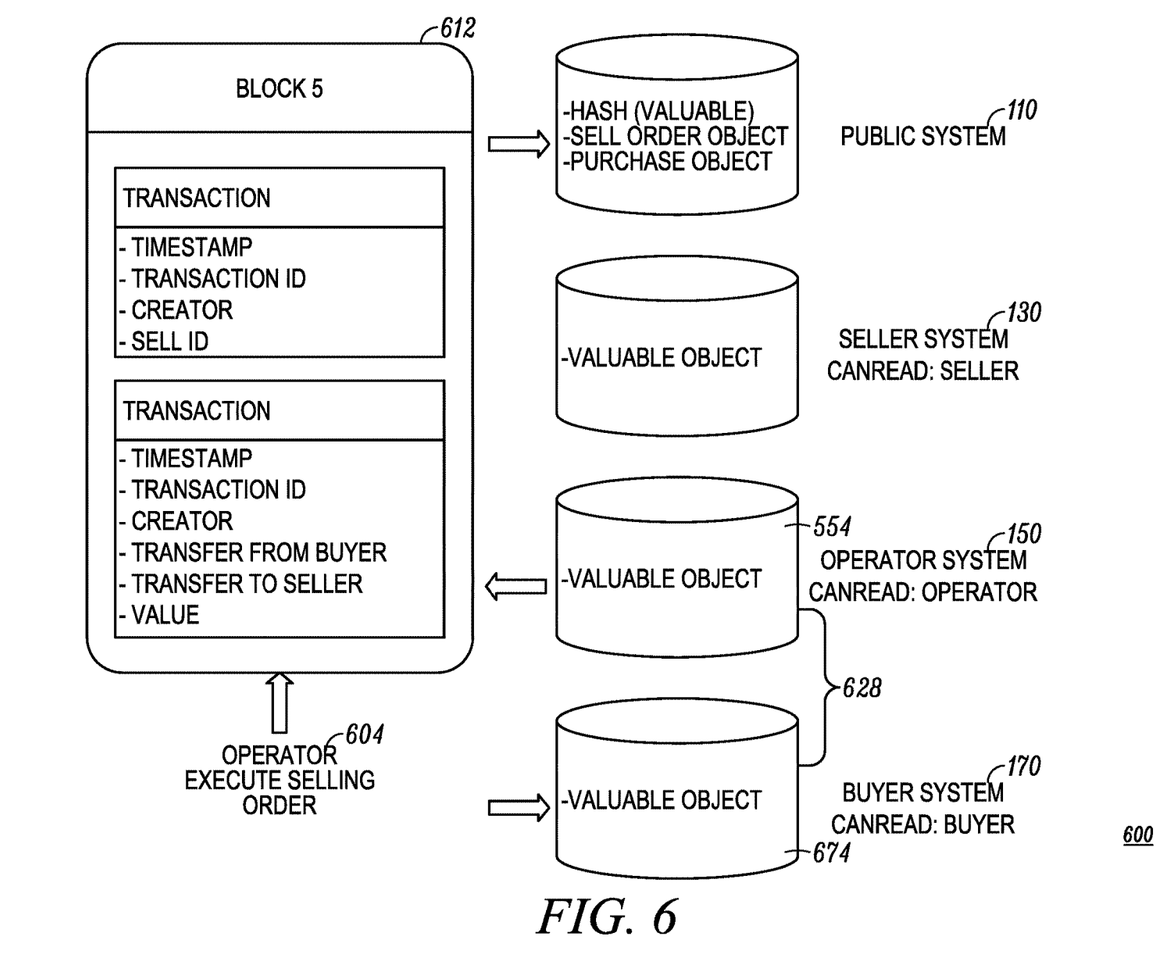

In FIG. 6, Block 5 612, the trusted operator indicated by the buyer and accepted by the seller executes the selling order, effectively copying the data object 554 from the Trust Operators system 150 to the buyer's private collection. The copying may include decrypting and re-encrypting as described above. The transaction may also include paying for the data access. Show is the data object 554 being copied from the Operator's Private Collection 554 to the seller's private collection 674. One copying method is based on the gossip protocol but it is important to note that there are other protocols that can be used as well.

Flow Chart

Figure 7:
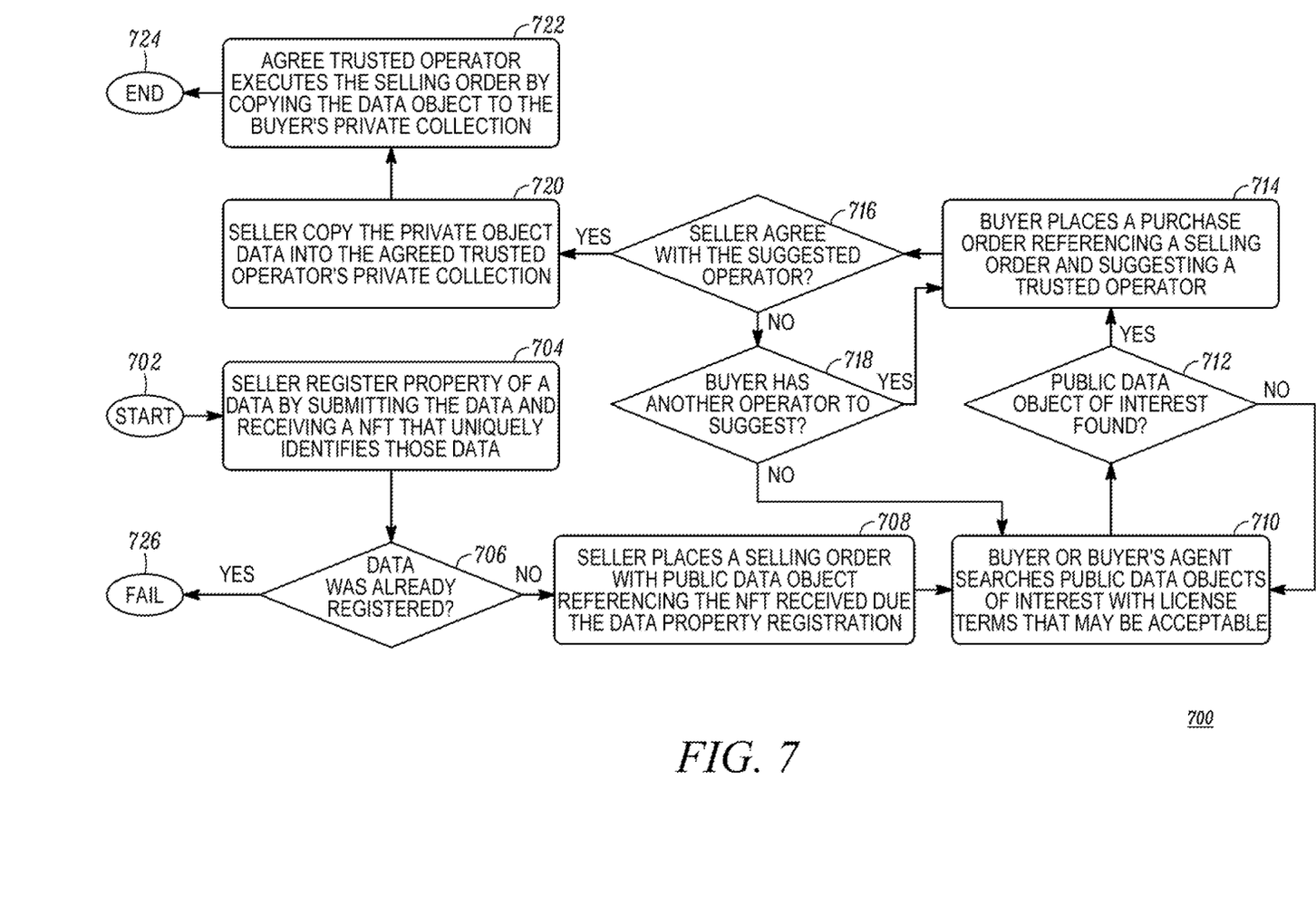
FIG. 7 is a high-level flow diagram for providing access to a private data object, in accordance with one aspect of the present invention.

FIG. 7 is a high-level flow diagram 700 for providing access to a private data object, according to one aspect of the present invention. The process begins in step 702 and immediately proceeds to step 704. In step 704 one of the sellers 130 registers a property of data on the blockchain 110 by providing public data object information. The blockchain 110 generates the unique token or NFT. In return for registering the public data object, the seller receives a unique token referencing the data object in the seller's private collection 133, 135, 137 to which access is being sold. The process continues to step 706.

In step 706, an inspection is made check if the data object was already registered. In the case that the data object was previously registered, the process fails in step 726 and sends the seller a notice that the data is already being offered. The process continues to step 708.

In step 708, the seller places a selling order with the public data object referencing the unique token in response to the data object being registered. The selling order typically includes the license conditions for a buyer. The process continues to step 710.

In step 710, the buyer or the buyer's agent searches public data objects of interest with license terms and conditions that may be acceptable. The process continues to step 712.

In step 712, a test is made to determine if a public data object of interest found. In the case no public data object is found, the process loops back to step 710. In the case a public data object is found, the process continues to step 714.

In step 714, the buyer places a purchase order referencing a selling order and suggesting a trusted operator. The process continues to step 716.

In step 716, a test is made to determine if seller agrees with the suggested trusted operator. If there is disagreement, the process continues to step 718. In 718 a test is made if the buyer has another trusted operator to suggest. If no trusted operator is suggested by the buyer, the process returns to step 710. Otherwise, in the case, the buyer has another trusted operator to suggest, the process continues to step 714. In the case that the seller agrees with the suggested operator, the process continues to step 720.

In step 720, the data object is copied from the seller's private collection to the trusted operator's (third-party) private collection, and the process continues to step 722. Alternately, the trusted operator may copy the data object directly from the seller's private collection to the buyer's private collection and therefore eliminating step 720 so that the trusted operator never has the object data stored in the trusted operator's private collection.

In step 722, the agreed trusted operator executes the selling order by copying the data object from the trusted operator's private collection to the buyer's private collection. The process ends in step 724.

Example Computer System

Figure 8:
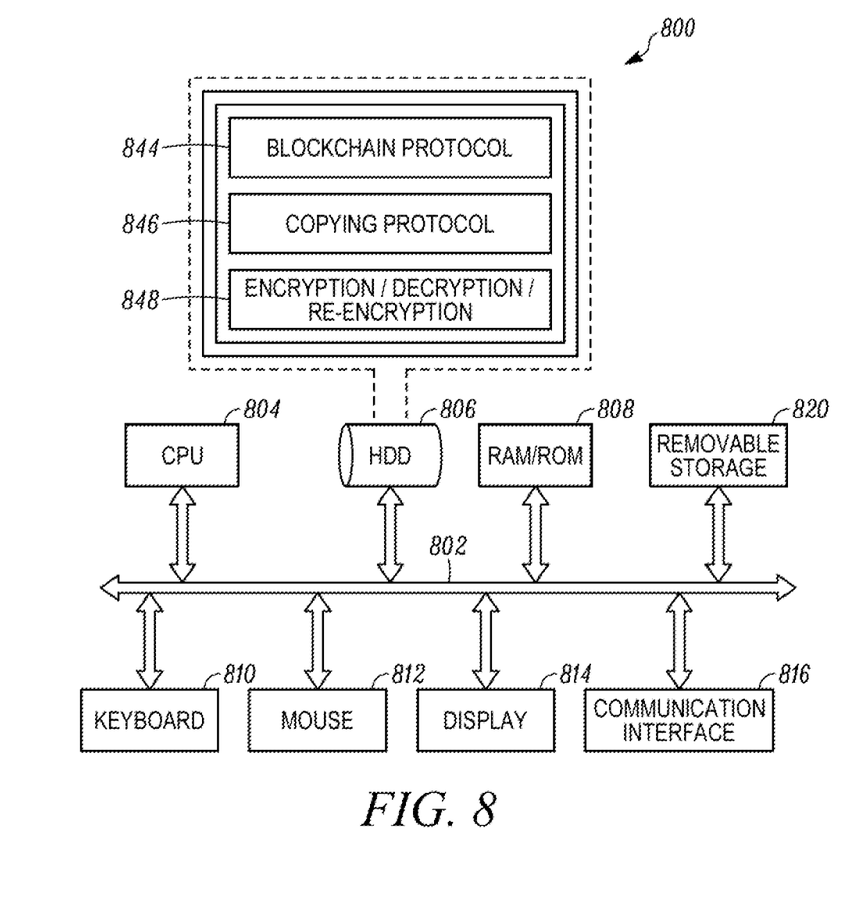
FIG. 8 is a functional block diagram illustration of a computer hardware platform, according to one aspect of the present invention.

FIG. 8 is a functional block diagram illustration of a computer hardware platform that can communicate with various networked components, according to one aspect of the present invention. In particular, FIG. 8 illustrates a particularly configured network or host computer platform 800, as may be used to implement the method to provide access to a private data object as shown in FIGS. 1 thru 7. FIG. 8 can implement any or part of systems 110, 130, 150, 170.

The computer platform 800 may include a central processing unit (CPU) 804, a hard disk drive (HDD) 806, random access memory (RAM) and/or read-only memory (ROM) 808, a keyboard 810, a mouse 812, a display 814, and a communication interface 816, which are connected to a system bus 802. The HDD 806 can include data stores.

In one embodiment, the HDD 806, has capabilities that include storing a program that can execute various processes, such as, for executing a blockchain protocol 844 to interface with blockchain 110, in a manner described herein. Another process may include a gossip protocol or other copying protocol 846 to seamlessly copy data from one private digital collection to another once access to the data object in the seller's private collection is granted by the collection's owner. Still, another process may be encryption, decryption, and re-encryption processes 848.

In one embodiment, a program, such as Apache™, can be stored for operating the system as a Web server. In one embodiment, the HDD 806 can store an executing application that includes one or more library software modules, such as those for the Java™ Runtime Environment program for realizing a JVM (Java™ virtual machine).

As will be appreciated by one skilled in the art, aspects of the present invention may be embodied as a system, method, or computer program product, such as a removable storage 820 at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Non-Limiting Examples

The flowchart and block diagrams in FIG. 1 through FIG. 8 illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The description of the present application has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand various embodiments of the present invention, with various modifications as are suited to the particular use contemplated.

What is claimed is:

1. A computer-implemented method for providing access to a private data object, the method comprising:
   storing a private data object off a digital ledger network in a seller's private digital collection;
   creating, by a seller, a private data register request, comprising of description of the private data object and the private data object itself;
   receiving, from the seller, the private data register request on the digital ledger network to sell access to a private data object;
   creating a cryptographic hash of the private data object;
   storing the cryptographic hash of the private data object on the digital ledger network;
   creating a public data object on the digital ledger network, the public data object comprising the description of the private data object and the cryptographic hash of the private data object;
   creating a cryptographic hash of the public data object;
   creating, by the seller, a public sell order on the digital ledger network to sell access to the private data object, the public sell order comprising the public data object, a purchase price to access the private data object and the cryptographic hash of the public data object;
   creating a public sell order object on the digital ledger network, the public sell object comprising a reference to the public data object and the purchase price to access the private data object;

creating a cryptographic hash of the public sell order object;

creating, by a buyer, on the digital ledger network a public buy order object to purchase access to the private data object, the public buy order object comprising a reference to the cryptographic hash of the public sell order object;

creating a cryptographic hash of the public buy order object;

creating an authorization of the buyer on the digital ledger network comprising a reference to the cryptographic hash of the public buy order object;

receiving the authorization of the buyer on the digital ledger network to authorize the purchase price to be debited from an account of the buyer;

updating the public sell order object on the digital ledger network to create an updated public sell order object comprising a public purchase object and a reference to the buyer;

the updated public sell order object comprising a reference to both the public sell order object and the public buy order object comprising the authorization of the buyer;

receiving an authorization of the seller on the digital ledger network to provide access to the private data object;

the updated public sell order object comprising a reference to the public sell order object comprising the authorization of the seller; and using a smart contract to copy the private data object stored in the seller's private digital collection and storing the private data object on a private digital collection of the buyer, and the seller's private digital collection and the private digital collection of the buyer are different digital collections that are stored off the digital ledger network.

2. The method of claim 1, further comprising:
the private data object is encrypted with a first encrypting key;
the creating the public buy order includes creating the public buy order with a proposed trusted third-party to validate a transaction, wherein the trusted third-party is any member of the digital ledger network;
the receiving the authorization of the seller includes receiving the authorization of the seller with an approval of the proposed trusted third party to validate the transaction; and
the copying by the trusted third-party includes decrypting the encrypted private data object with a first decrypting key by the trusted third party, re-encrypting the decrypted private data object with a second encryption key by the trusted third party, and copying by the trusted third party the re-encrypted private data object stored in the seller's private digital collection.

3. The method of claim 2, wherein the computer-implemented method is performed by a same entity that manages the third-party.

4. The method of claim 2, wherein the seller's private digital collection, the buyer's private digital collection, and the third-party are different entities.

5. The method of claim 2, wherein the third-party is one of a plurality of third-parties, and the third-party is selected by the at least one of the seller, the buyer, or both.

6. The method of claim 2, wherein the seller and the buyer agree on the third party selected.

7. The method of claim 2, wherein the third-party is one of the buyer or the seller.

8. The method of claim 1, wherein in response to the authorization of the seller, copying the private data object stored in the seller's private digital collection to a third-party in which the private data object is encrypted with a first encrypting key, and decrypting the private data object using a first decrypting key of the seller, and re-encrypting the private data object using a second encrypting key of the buyer and storing the re-encrypted private data object on a buyer's private digital collection.

9. The method of claim 1, wherein the private data object is at least one of a non-fungible token, data from a sensor, and medical records.

10. The method of claim 1, wherein the private data object is at least one of a data from a sensor, a medical record, images, videos, or any other digital content and is referenced into the digital ledger network as a non-fungible token (NFT).

11. The method of claim 1, wherein the step of receiving the public buy order from the buyer to purchase access to the private data object further comprises:
searching, by the buyer, over the digital ledger network, for public selling orders.

12. The method of claim 1, wherein the step of receiving the public buy order from the buyer to purchase access to the private data object further comprises:
receiving, from the buyer, a data purchase interest request, on the digital ledger network, the data purchase interest request containing conditions to purchase access to the private data object; and
in response to receiving the data purchase interest request, receiving, from a third-party agent on the digital ledger network, a recommendation of selling orders that matches the conditions to purchase access to the private data object.

13. A method on a computer system for providing access to a private data object, the method comprising:
storing a private data object off a digital ledger network in a seller's private digital collection;
creating, by a seller, a private data register request, comprising of description of the private data object and the private data object itself;
receiving, from the seller, the private data register request on the digital ledger network to sell access to a private data object;
creating a cryptographic hash of the private data object;
storing the cryptographic hash of the private data object on the digital ledger network;
creating a public data object on the digital ledger network, the public data object comprising the description of the private data object and the cryptographic hash of the private data object;
creating a cryptographic hash of the public data object;
creating, by the seller, a public sell order on the digital ledger network to sell access to the private data object, the public sell order comprising the public data object, a purchase price to access the private data object and the cryptographic hash of the public data object;
creating a public sell order object on the digital ledger network, the public sell object comprising a reference to the public data object and the purchase price to access the private data object;
creating a cryptographic hash of the public sell order object;
receiving from the seller, the buyer or both, a selection for a third-party operator to manage a purchase-sale transaction between the seller and the buyer;

receiving authorization from both the seller and the buyer that the third-party operator is an authorized third-party operator to manage the purchase-sale transaction;

creating, by a buyer, on the digital ledger network a public buy order object to purchase access to the private data object, the public buy order object comprising a reference to the cryptographic hash of the public sell order object;

creating a cryptographic hash of the public buy order object;

creating an authorization of the buyer on the digital ledger network comprising a reference to the cryptographic hash of the public buy order object;

receiving the authorization of the buyer on the digital ledger network to authorize the purchase price to be debited from an account of the buyer;

updating the public sell order object on the digital ledger network to create an updated public sell order object comprising a public purchase object and a reference to the buyer;

the updated public sell order object comprising a reference to both the public sell order object and the public buy order object comprising the authorization of the buyer;

receiving an authorization from the seller on the digital ledger network to provide access to the private data object;

the updated public sell order object comprising a reference to the public sell order object comprising the authorization of the seller; and using a smart contract to copy the private data object stored in the seller's private digital collection and storing the private data object on a private digital collection of the buyer, and the seller's private digital collection and the private digital collection of the buyer are different digital collections that are stored off the digital ledger network.

14. The method of claim 13, wherein in response to the authorization of the seller, the purchase price to be debited from the account of the buyer is divided into two payment parts, a first payment part paid to the third-party operator and a second payment part paid to the seller.

15. The method of claim 13, wherein the method is performed by the same entity that manages the third-party operator.

16. The method of claim 13, wherein the seller's private digital collection, the buyer's private digital collection, and the third-party operator are different entities.

17. The method of claim 13, wherein the third-party is one of a plurality of third-parties, and the third-party operator is selected by the at least one of the seller, the buyer, or both.

18. The method of claim 17, wherein the seller and the buyer agree on the third party operator selected.

19. The method of claim 17, wherein the third-party operator is one of the buyer or the seller.

20. A digital ledger system, comprising:
a processor device; and
a memory operably coupled to the processor device and storing computer-executable instructions causing:
storing a private data object off a digital ledger network in a seller's private digital collection;
creating, by a seller, a private data register request, comprising of description of the private data object and the private data object itself;
receiving, from the seller, the private data register request on the digital ledger network to sell access to a private data object;
creating a cryptographic hash of the private data object;
storing the cryptographic hash of the private data object on the digital ledger network;
creating a public data object on the digital ledger network,—the public data object comprising the description of the private data object and the cryptographic hash of the private data object;
creating a cryptographic hash of the public data object;
creating, by the seller, a public sell order on the digital ledger network to sell access to the private data object, the public sell order comprising the public data object, a purchase price to access the private data object and the cryptographic hash of the public data object;
creating a public sell order object on the digital ledger network, the public sell object comprising a reference to the public data object and the purchase price to access the private data object;
creating a cryptographic hash of the public sell order object;
creating, by a buyer, on the digital ledger network a public buy order object to purchase access to the private data object, the public buy order object comprising a reference to the cryptographic hash of the public sell order object;
creating a cryptographic hash of the public buy order object;
creating an authorization of the buyer on the digital ledger network comprising a reference to the cryptographic hash of the public buy order object;
receiving the authorization of the buyer on the digital ledger network to authorize the purchase price to be debited from an account of the buyer;
updating the public sell order object on the digital ledger network to create an updated public sell order object comprising a public purchase object and a reference to the buyer;
the updated public sell order object comprising a reference to both the public sell order object and the public buy order object comprising the authorization of the buyer;
receiving an authorization from the seller on the digital ledger network to provide access to the private data object;
the updated public sell order object comprising a reference to the public sell order object comprising the authorization of the seller; and
using a smart contract to copy the private data object stored in the seller's private digital collection and storing the private data object on a private digital collection of the buyer, and the seller's private digital collection and the private digital collection of the buyer are different digital collections that are stored off the digital ledger network.

* * * * *